United States Patent [19]

Koide et al.

[11] Patent Number: 5,290,685

[45] Date of Patent: Mar. 1, 1994

[54] METHOD FOR SEPARATION AND CONCENTRATION OF PHOSPHOPEPTIDES

[75] Inventors: Kaoru Koide; Takashi Fukushima, both of Tokyo; Tamotsu Kuwata, Saitama; Koki Itoyama, Shizuoka; Fumio Miyazawa, Kanagawa, all of Japan

[73] Assignee: Meiji Milk Products Company Limited, Tokyo, Japan

[21] Appl. No.: 53,808

[22] Filed: Apr. 29, 1993

Related U.S. Application Data

[63] Continuation of Ser. No. 651,153, Feb. 6, 1991, abandoned.

[30] Foreign Application Priority Data

Feb. 22, 1990 [JP] Japan ................. 2-39721

[51] Int. Cl.$^5$ ............... C12P 21/00; C07K 3/12; A61K 37/16
[52] U.S. Cl. ................. 435/68.1; 435/272; 514/7
[58] Field of Search ............ 435/68.1, 272; 514/7

[56] References Cited

U.S. PATENT DOCUMENTS

| | | | |
|---|---|---|---|
| 4,358,465 | 11/1982 | Brule et al. | 435/68.1 |
| 4,361,587 | 11/1982 | Brule et al. | 435/68.1 |
| 4,462,990 | 7/1984 | Jolles et al. | 435/68.1 |
| 4,495,176 | 1/1985 | Brule et al. | 435/68.1 |
| 4,740,462 | 4/1988 | Brule et al. | 435/68.1 |
| 4,777,243 | 10/1988 | Jolles et al. | 574/7 |
| 4,816,398 | 3/1989 | Brule et al. | 435/68.1 |
| 4,835,265 | 5/1989 | Muzzavelli | 536/18.7 |
| 4,879,340 | 11/1989 | Moriguchi et al. | 530/351 |
| 4,906,616 | 3/1990 | Gilchrist et al. | 435/272 |
| 4,980,450 | 12/1990 | Brule et al. | 530/360 |
| 4,997,914 | 3/1991 | Kawakami et al. | 530/366 |
| 5,014,628 | 5/1991 | Reynolds | 435/360 |
| 5,028,589 | 7/1991 | Brule et al. | 435/68.1 |

FOREIGN PATENT DOCUMENTS

| | | | |
|---|---|---|---|
| 56-123921 | 9/1981 | Japan . | |
| 58-170440 | 10/1983 | Japan . | |
| 59-159793 | 9/1984 | Japan . | |
| 1-16420 | 3/1989 | Japan . | |
| 8201131 | 4/1982 | World Int. Prop. O. | 514/7 |
| 8707615 | 12/1987 | World Int. Prop. O. | 435/68.1 |

OTHER PUBLICATIONS

Yoshida et al. (1989) *Chem. Eng. J.*, 41(1), B11-B15, in *Chem Abstr.*, 111, 387, Abst. No. 74122y.

West, D. W., "A simple method for the isolation of a phosphopeptide from bovine $\alpha_{s1}$-casein", (1977) *J. Dairy Res.*, 44(32), 373-376.

Manson, W., and Annan, W. D. "The Structure of a Phosphopeptide Derived from $\beta$-Casein", Arch. Biochem., 145, 15-26 (1971).

Naito, H. and Suzuki, H., "Further Evidence for the Formation in vivo of Phosphopeptide in the Intestinal Lumen from Dietary $\beta$-Casein", Arg. Biol. Chem., 38(8), 1543-1545 (1974).

Lee, Y. S., Noguchi, T. and Naito, H., "Phosphopeptides and soluble calcium in the small intestine of rats given a casein diet", British J. of Nutrition, 43, 457-467 (1980).

*Primary Examiner*—Douglas W. Robinson
*Assistant Examiner*—Jon P. Weber
*Attorney, Agent, or Firm*—Browdy and Neimark

[57] ABSTRACT

The present invention relates to a method for separating and concentrating acidic peptide, especially phosphopeptide having a phosphoserine residue, from a peptide mixture prepared by digesting casein with protease.

12 Claims, No Drawings

METHOD FOR SEPARATION AND CONCENTRATION OF PHOSPHOPEPTIDES

This application is a continuation of application Ser. No. 07/651,153, filed Feb. 6, 1991, now abandoned.

FIELD OF THE INVENTION

The present invention relates to a method for separating and concentrating acidic peptides, especially phosphopeptide having a phosphoserine residue, from a peptide mixture prepared by digesting casein with protease.

More particularly, the present invention relates to a method for separation and concentration of these peptides either without using any organic solvent such as ethyl alcohol, pyridine, etc., or without adding calcium, iron, etc. In addition, the present invention is also applicable not only to trypsin hydrolysates of casein which are casein phosphopeptides (hereafter referred to as CPP) generally termed as plural kinds of peptides containing a phosphoserine residue, but also widely to hydrolysates with proteases other than trypsin.

PRIOR ART

Several methods were established around 1970 for preparing casein-derived phosphopeptides on a laboratory scale For example, W. Manson and W. D. Annan precipitate and fractionate phosphopeptides by adding barium chloride and ethyl alcohol to a soluble fraction of pH 4.6 in the solution obtained by cleaving β-casein with trypsin at pH 8 at 20° C. (Arch. Biochem., 145, 15-26 (1971)).

On the other hand, Naito and Suzuki roughly fractionate a solution of trypsin digestion products of β-casein by gel filtration, pass the fraction through an ion exchanger (DOWEX 50-X2) column and then carry out the elution with pyridine-acetate buffer (pH 2.5, 0.2N pyridine) to fractionate phosphopeptides, etc. (Arg. Biol. Chem., 38 (8), 1543-1545 (1974)).

Also West adjusts the pH of a solution of α-casein treated with trypsin to 2 to remove the precipitates, then applies the filtrate to gel filtration (Sephadex G-25M), collects a large molecular fraction eluted in Void Volume and then passes the fraction through an anionic exchanger (DEAE Sepharose A50) to adsorb phosphopeptides to the anionic exchanger.

However, these methods are basically to prepare CPP for the purpose of research or to confirm the presence or purity of CPP. In order to industrialize these methods as preparing food materials, inappropriate reagents such as barium chloride, pyridine, etc. are used, or operations which are difficult for scaling up for industrialization are involved.

On the other hand, for the purpose of preparation on a large scale, it has been proposed to separate phosphopeptides from other peptides through an ultrafiltration membrane, utilizing the property of phosphopeptides that phosphopeptides from peptides formed by decomposition of casein with protease do not precipitate but from a large aggregate by the addition of minerals such as calcium (Japanese Patent Application Laid-Open No. 123921/81).

Furthermore, it is known to precipitate and isolate phosphopeptides by adding calcium and ethyl alcohol or by adding ferric chloride to the cleavage products of casein with trypsin (Japanese Patent Application Laid-Open Nos. 170440/83 and 159793/84).

PROBLEMS TO BE SOLVED BY THE INVENTION

In order to use phosphopeptides as food materials or medical materials, incorporated of barium salt should be avoided. Therefore, the method of manson and Annan using barium chloride in the prior art described above is not suitable.

Furthermore, the method using ethyl alcohol requires large quantities of expensive ethyl alcohol. In the case of the treatment on a large scale, problems are, thus, encountered especially from economic and safety considerations. In addition, since CPP is also known to be a calcium absorption accelerator (British J. of Nutrition, 43, 457-467 (1980)), minerals such as calcium and the like are used in combination separately from other sources, where phosphopeptides are used in food materials as the calcium absorption accelerator; therefore, it is preferred that minerals such as calcium are not contained in phosphopeptides. In such a case, it is recommendable to supply phosphopeptides in the market in a calcium-free or iron-free state, because its application area may be broadened and hence its commercial value becomes high.

On the other hand, the laboratory scale methods described above involve various problems. Firstly, the method using the barium salt is inapplicable to food materials. Turning next to the method using gel filtration in combination with ion exchange column chromatography, it is impossible to apply gel filtration to a large scale process at this time.

Further in the latter method, anionic exchange resin principally has affinity for phosphopeptides having a phosphoserine residue. However, casein itself is an acidic protein and protease digestion products also keep affinity for anionic exchanger as a whole. Therefore, in order to isolate phosphopeptides from the whole peptides, severe selectivity is required. In actuality, when used singly, most anionic exchange resins have an extremely weak adsorption to phosphopeptides. Even though an anionic exchange resin having affinity for a large molecular substance such as phosphopeptides is used, the selectivity of adsorption is weak. In addition, adsorbability is weak in a narrow pH range which gives a relatively strong selectivity. Accordingly, the method is not applicable, unless phosphopeptides are prepared from an extremely diluted peptide mixture solution at the sacrifice of yield or production efficiency. Moreover, not only an ionic interaction takes part in the bond between an ordinary anionic exchange resin and peptide but hydrophobic bonds, etc. also strongly take part therein. Therefore, in order to sufficiently elute and recover a substance once adsorbed, it is necessary to use a solvent type eluent such as pyridine, or add a salt of a very high concentration, etc., which makes its application to practical preparation impossible.

MEANS FOR SOLVING THE PROBLEMS

The present invention relates to a method for separation and concentration of phosphopeptides which comprises treating a raw material comprising casein and/or a casein-based raw material with protease, adsorbing the resulting protein digestion products onto a cross-linked chitosan-formed substance and then desorbing the protein digestion products. The present invention also relates to the method wherein the adsorption is carried out in the pH range of 1.5 to 5.0.

An object of the present invention is to solve the foregoing defects and to develop a large scale method which can efficiently isolate and recover phosphopeptides free of harmful or unnecessary minerals such as Ba, Ca, Fe, etc., without using expensive raw materials such as ethyl alcohol.

Another object of the present invention is not to develop merely an industrial method suited for a large scale production but is to develop a large scale method in which devices already installed in the dairy industry or food industry can be used, without installing new apparatuses.

Therefore, the present inventors have made various investigations on an economical preparation by concentrating and isolating phosphopeptides from protease digestion products of casein on an industrial scale, using devices conventionally installed in the dairy industry or food industry, without installing new apparatuses, without using any reagents unsuitable from a hygienic consideration. As a result, it has been found that the objects can be achieved by the use of a separating agent (hereafter crosslinked chitosan molding) prepared by molding chitosan (polysaccharide comprising 2-amino-2-deoxy-D-glucose as a main component), followed by a crosslinking treatment. The present invention has thus been accomplished.

The chitosan-based crosslinked chitosan molding used in the present invention can be obtained by molding chitosan, then subjecting the molding to a crosslinking treatment, thereby imparting acid resistance to the molding.

The chitosan molding may be of particles, layers, fibers, etc. but in view of surface area or operation upon use, the chitosan is preferably comprised of porous particles.

The porous particles of chitosan may be obtained by the method disclosed in Japanese Patent Publication No. 16420/89. That is, the porous particles are obtained by dissolving lower molecular weight chitosan having an average molecular weight of 10,000 to 230,000 in an acidic solution such as an acetic acid solution, etc. to obtain a chitosan acidic solution of 2 to 20%, adding dropwise the solution onto a basic solution such as a sodium hydroxide solution, etc. to regenerate and solidify, and then thoroughly washing with water.

In this case, the particle diameter of the porous particles can be controlled by the nozzle diameter of a dropping nozzle of the chitosan acidic solution, a discharge pressure, and the like.

The particle diameter of the chitosan porous particles is not particularly limited but is preferably 0.1 to 1.0 mm$\phi$ in the present invention, from aspects of operation and adsorption amount.

The crosslinking agents used for the purpose of imparting acid resistance to the thus obtained chitosan molding may be those which are reactive with the amino group of chitosan and examples thereof include diisocyanates, dialdehydes, dicarboxylic acid derivatives, diepoxy compounds, etc. In view of ion exchange volume and reactivity, it is preferred to use diepoxy compounds shown by the following formulae.

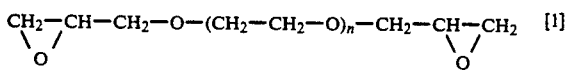 [1]

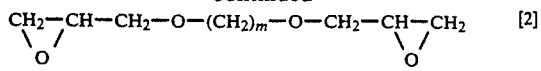 [2]

(wherein n=1 to 10, m=3 to 10)

In the formulae above, examples of [1] include ethylene glycol diglycidyl ether, diethylene glycol diglycidyl ether, triethylene glycol diglycidyl ether, etc.; and examples of [2] include trimethylene glycol diglycidyl ether, tetramethylene glycol diglycidyl ether, hexamethylene glycol diglycidyl ether, etc.

When the crosslinking degree in this case is excessively high, a pore diameter becomes small, so that a diffusion rate of CPP in the particles decreases: when the crosslinking degree is too low, strength and acid resistance decrease. Therefore, it is preferred to treat with the crosslinking agent in a range of 5 to 30 mol % per chitosan residue.

As casein which is used as a raw material in the present invention, a variety of acid casein, sodium caseinate, calcium caseinate, etc. are most preferred, but unpurified casein such as milk, skimmed milk, etc. may also be used. Concentrates or treated matters such as residues after ultrafiltration thereof, etc. may also be advantageously used. Furthermore, unpurified phosphopeptides or various phosphocaseinates, etc. may also be used. Thus, casein-containing or casein-based various raw materials may be widely used.

In the present invention, such raw materials are treated with protease to produce protein digestion products. This step may be carried out as in the step for preparing CPP using trypsin as protease. For example, after acid casein is neutralized, or sodium caseinate is dissolved to form a solution of about 1 to about 10%, protease is added to the solution and the mixture is allowed to stand at pH of 8.0, a temperature of 30° to 45° C. for 3 to 24 hours. From economical consideration, it is preferred to adjust pH and a ratio of soluble N/total N after completion of the enzyme reaction to 4.6 and 0.8 or more, respectively.

In the present invention, protease is not limited only to purified trypsin as in the case of CPP but there may be used protease such as animal-derived enzyme such as pancreatin, pepsin, chymotrypsin, etc.; plant-derived enzyme such as papain, bromelain, ficin, etc.; microorganism-derived enzyme such as mold, yeast, bacterial protease, etc.

From a mixture solution of various peptides prepared by the digestion with protease of casein or material containing casein chiefly, acid peptides (chiefly phosphopeptides) can be adsorbed in a very high selectivity and adsorption rate onto a separating agent, i.e., the crosslinked chitosan molding as above-prepared. Upon elution of phosphopeptides an elution rate of about 80% or more can be easily achieved merely by varying pH. Where the elution rate should be as close as 100% at one, this can be achieved by adding a small amount of sodium chloride.

While it is not sufficiently clarified yet that the crosslinked chitosan molding is excellent for phosphopeptides, it is assumed that positively charged amino groups are uniformly dispersed with appropriate intervals, hydrophilic property of the skeleton excluding the positively charged portions is strong, etc. would be effective.

A concentration of the peptide solution mixture is not particularly limited but as a criterion of the concentration, the concentration obtained after the enzyme reaction is completed may be used as it is; or, if necessary, it is preferable to dilute the same to about 0.1 to about 5% of the solid content.

In order to selectively adsorb phosphopeptides from the solution of casein and enzyme digestion products, it is most important to control pH. The pH value should be in the range of 1.5 to 5.0, more preferably, 2.5 to 4.5.

At pH of greater than 5.0, adsorption capability is poor since both primary amino groups and secondary amino groups in the crosslinked chitosan molding have extremely small dissociation and their ionic interaction with phosphopeptides is weak. In addition, many peptides other than phosphopeptides in the casein enzyme digestion solution are negatively charged in such a high pH range, so that selectivity of adsorption becomes low. Conversely at pH below 1.5, charge state in most of the phosphopeptides is either extremely low or the same symbol as that of the crosslinked chitosan molding, so that no adsorption occurs.

The adsorption temperature may be at room temperature. Even in an ordinary variation of temperature, any great change in adsorption rate is not observed.

The adsorption of phosphopeptides begins at the moment when the enzyme digestion solution of casein is brought into contact with the crosslinked chitosan molding. However, in order to render the adsorption amount the maximum, it is preferred to take a reaction time of 10 to 30 minutes after pH adjustment.

From the thus prepared phosphopeptide-adsorbed matter, phosphopeptides can be easily isolated and separated by conventional solid-liquid separation methods. For the solid-liquid separation, centrifugation, decantation, filtration, membrane filtration, etc. may be used but the separation is not limited only to these techniques.

The crosslinked chitosan molding to which the acid peptide prepared as described above is adsorbed is treated to discharge the solution containing non-adsorbed peptides through a screen equipped in a reaction vessel and then, if necessary, wash off the crosslinked chitosan molding with water, and finally goes into the step of eluting phosphopeptides.

That the desorption of most phosphopeptides can be effected simply by adjusting pH is characteristic of the use of the crosslinked chitosan molding. More specifically, the crosslinked chitosan molding after the non-adsorbed fraction is discharged is dispersed in water and its pH is adjusted with an acid or an alkali to 1.5 or less or 5 or more.

Only by adjusting pH, about 10 to about 20% of the phosphopeptides adsorbed may remain in some occasion; in this case, the residual peptides increase by using repeatedly the crosslinked chitosan molding. In such a case, by adding approximately 0.2 to 1 mol/l of sodium chloride aqueous solution, the residual peptides can be eluted out and recovered.

As an apparatus for adsorption and desorption (elution) of the phosphopeptides using the crosslinked chitosan molding, a stainless or synthetic polymer-made column packed with the crosslinked chitosan molding may be used but it is sufficient to use a simple system in which the enzyme digestion solution of casein is introduced into a tank or fermenter ordinarily used in the dairy industry and a definite amount of the crosslinked chitosan molding is incorporated therein.

The eluted solution containing the phosphopeptides is concentrated and sterilized; the concentrate may be packed to provide for use as it is, or the concentrate may be spray dried to form powder. Where large quantities of salt are used during the course of elution, desalting may be performed by ion exchange or electric dialysis, etc. followed by concentration and drying.

Next, preparation of the crosslinked chitosan molding used in the present invention and the isolation and concentration of the phosphopeptides are described in detail in the following examples. Test examples are also shown.

EXAMPLE 1

After 1.8 kg of low molecular weight chitosan having a deacetylation degree of 82% and a mean molecular weight of 42,000 was dissolved in 27.9 kg of 3% acetic acid solution, the resulting solution was added dropwise to a solution mixture of sodium hydroxide:ethanol:water=6.5:20:73.5 through a nozzle having a pore diameter of 0.15 mm$\phi$ to solidify and regenerate. Then, the product was washed until it became neutral. Thus, 30 l (wet state) of the chitosan molding having a mean particle diameter of 0.3 mm$\phi$ was obtained.

To 30 l (wet state) of the chitosan molding obtained were added 15 l of isopropyl alcohol and 300 g of ethylene glycol diglycidyl ether. After reacting at 70° C. for 2 hours, the reacted molding was washed with water to give 30 l of the crosslinked chitosan molding having a specific surface area of 85.2 m$^2$/g and an ion exchange volume of 0.45 meq/ml.

Separately, the pH of 100 kg of 5% casein solution prepared from acid casein was adjusted to 8 and using swine trypsin (Trypsin-6S, Novo Co., Ltd.), casein was decomposed until the nitrogen components insoluble at pH 4.6 became 10% or less. The precipitates caused at pH of 4.6 were removed by centrifugation; about 3,960 g of peptide containing about 450 g of phosphopeptides was noted in the solution. The solution was transferred to a reaction tank equipped with a screen at the lower part thereof. After 30 l (wet state) of the crosslinked chitosan molding prepared as described above was put in the solution, pH was adjusted to 3.5 with hydrochloric acid. The system was allowed to stand for 30 minutes; and then the liquid was discharged through the screen, whereby only the crosslinked chitosan molding remained. After the crosslinked chitosan molding was washed with 50 kg of water, 100 kg of water was charged in the tank and pH was adjusted to 1.5 while gently stirring together with the crosslinked chitosan molding, followed by being allowed to stand for 20 minutes, thereby the acid peptides mainly composed of phosphopeptides being eluted out of the crosslinked chitosan molding. About 520 g of the solids mainly composed of the peptides were contained in the eluate; among them, the phosphopeptides were about 320 g.

EXAMPLE 2

To 30 l (wet state) of the chitosan molding having a mean particle diameter of 0.3 mm$\phi$ obtained in a manner similar to Example 1 were added 15 l of isopropyl alcohol and 325 g of trimethylene glycol diglycidyl ether. After reacting at 70° C. for 2 hours, the reacted molding was washed with water to give 30 l of the crosslinked chitosan molding having a specific surface area of 85.5 m$^2$/g and an ion exchange volume of 0.48 meq/ml.

A solution of the digestion product of casein with trypsin was prepared under the same conditions as in Example 1 and the solution was transferred to the same reaction tank. After 30 l of the crosslinked chitosan molding prepared as described above was put in the solution, pH was adjusted to 3.5 with hydrochloric acid. The system was allowed to stand for 30 minutes; and then the liquid was discharged through the screen, whereby only the crosslinked chitosan molding remained. After the crosslinked chitosan molding was washed with 50 kg of water, 100 kg of water was charged in the tank and pH was adjusted to 7.3 while gently stirring together with the crosslinked chitosan molding, followed by being allowed to stand for an hour, thereby the acid peptides being eluted out of the crosslinked chitosan molding. About 590 g of the solids mainly composed of the peptides were contained in the eluate; among them, the phosphopeptides were about 360 g.

TEST EXAMPLES

Test examples are shown to compare the ability of adsorbing phosphopeptides between the crosslinked chitosan molding and known ion exchange resins and their elution behaviors.

A solution of the digestion products of casein with trypsin containing 0.45% of phosphopeptides was taken by 80 ml each in 5 beakers of 100 ml. To each beaker was charged 5 g each of the crosslinked chitosan molding prepared in Example 1 and four kinds of known ion exchange resins. After pH was adjusted to 3.5 with hydrochloric acid, the system was allowed to stand for 30 minutes. Using a glass funnel as a filter, the resin and the discharge liquid (A) containing non-adsorbed fraction were separated from each other. A volume of (A) and phosphopeptide content in (A) were determined. An adsorption rate of the phosphopeptides was calculated according to the following equation:

$$\text{Adsorption rate (\%)} = \frac{225 \text{ mg} - \text{mg of phosphopeptides in discharge liquid } (A)}{225 \text{ mg}} \times 100$$

Next, the crosslinked chitosan molding and ion exchange resins remained on the glass filter were restored to beakers of 100 ml, respectively. After 50 ml of water was added into each beaker, pH was adjusted to 1.5 with hydrochloric acid. The system was kept for 30 minutes as it was, to elute the adsorbed phosphopeptides. Then, the resin and the eluate (B) were separated from each other using a glass funnel, and the phosphopeptide content in the eluate (B) was determined. An elution rate was calculated according to the following equation:

$$\text{Elution rate (\%)} = \frac{\text{mg of phosphopeptides in eluate } (B)}{225 \text{ mg} - \text{mg of phosphopeptides in discharge liquid } (A)} \times 100$$

The results are summarized in the following table.
The results reveal that the crosslinked chitosan molding is extremely superior in efficiency.

| | Skeleton | Adsorption Rate (%) | Elution Rate (%) |
|---|---|---|---|
| I Crosslinked chitosan molding obtained in Example 1 | chitosan type | 88 | 82 |
| II DIAION PA 308 (made by Mitsubishi Chemical Industry Co., Ltd.) | styrene type | 62 | 4 |
| III AMBERLITE IRA 35 (made by Organo Co.) | acryl type | 55 | 12 |
| IV AMBERLITE IR 45 (made by Organo Co.) | styrene type | 53 | 10 |
| V DIAION WA 30 (made by Mitsubishi Chemical Industry Co., Ltd.) | styrene type | 62 | 5 |

EFFECTS OF THE INVENTION

According to the present invention, casein-derived phosphopeptides can be produced extremely economically on an industrial scale, without using any organic solvent such as ethanol, pyridine, etc., utilizing facilities already installed, in such a form free of calcium or iron that the phosphopeptides are expected to accelerate the absorption of calcium or iron in vivo.

The thus obtained phosphopeptides can be used over wide areas including food materials, functional foodstuffs, nutrients, etc.

What is claimed is:

1. A method for separating phosphopeptides from an aqueous solution containing casein peptides, wherein said aqueous solution was prepared by treating casein with an enzyme selected from the group consisting of trypsin, pepsin, chyrotrypsin and papain, comprising:
   (a) adjusting the pH of the aqueous solution of casein peptides to a pH value of from 1.5 to 5.0;
   (b) contacting the aqueous solution of casein peptides with a crosslinked chitosan molding and adsorbing said casein peptides onto said crosslinked chitosan molding;
   (c) desorbing phosphopeptides from said crosslinked chitosan molding under pH conditions of less than 1.5 or more than 5.0 to obtain a solution containing phosphopeptides; and
   (d) concentrating the solution containing phosphopeptides obtained in step (c) to give a concentrated solution of phosphopeptides and optionally spray-drying further said concentrated solution to form powdered phosphopeptides.

2. The method according to claim 1 wherein said crosslinked chitosan molding is in the form of porous particles.

3. The method according to claim 2 wherein said porous particles have a diameter of from 0.1 to 1.0 mm.

4. The method according to claim 2 wherein said crosslinked chitosan molding is prepared by crosslinking chitosan with a diepoxy compound selected from compounds having the following formulae:

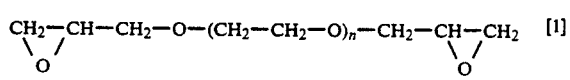

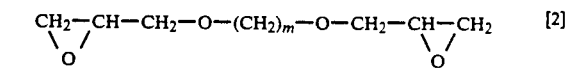

wherein n is from 1 to 10 and m is from 3 to 10.

5. The method according to claim 1 wherein the casein source is selected from the group consisting of acid casein, sodium caseinate, and calcium caseinate.

6. The method according to claim 1 wherein, after said phosphopeptides are desorbed from said crosslinked chitosan molding, said crosslinked chitosan molding is separated from the solution phosphopeptides by centrifugation, decantation, filtration, or membrane filtration.

7. The method according to claim 1 wherein said phosphopeptides have a phosphoserine residue.

8. The method according to claim 4 wherein said diepoxy compound is selected from the group consisting of ethylene glycol diglycidyl ether, diethylene glycol diglycidyl ether, triethylene glycol diglycidyl ether, trimethylene glycol diglycidyl ether, tetramethylene glycol diglycidyl ether, and hexamethylene glycol diglycidyl ether.

9. The method according to claim 1 wherein said phosphopeptides are desorbed from said crosslinked chitosan molding by adding water and adjusting the pH to less than 1.5.

10. A method for separating phosphopeptides from an aqueous solution containing casein peptides, wherein said aqueous solution was prepared by treating casein with an enzyme selected from the group consisting of trypsin, pepsin, chymotrypsin and papain, consisting essentially of:
 (a) adjusting the pH of the aqueous solution of casein phosphopeptides to a pH value of from 1.5 to 5.0;
 (b) contacting the aqueous solution of casein peptides with a crosslinked chitosan molding and adsorbing said casein peptides onto said crosslinked chitosan molding;
 (c) desorbing phosphopeptides from said crosslinked chitosan molding under pH conditions of less than 1.5 or more than 5.0 to obtain a solution containing phosphopeptides; and
 (d) concentrating the solution containing phosphopeptides obtained in step (c) to give a concentration solution of phosphopeptides, and optionally further spray-drying said concentration solution to form powdered phosphopeptides.

11. The method according to claim 10 wherein the pH value of step (a) is from 2.5 to 4.5.

12. The method according to claim 10 wherein the phosphopeptides have a phosphoserine residue.

* * * * *